United States Patent [19]

Tataria et al.

[11] 4,169,779

[45] Oct. 2, 1979

[54] ELECTROCHEMICAL CELL FOR THE DETECTION OF HYDROGEN SULFIDE

[75] Inventors: Harshad Tataria, Miami, Fla.; Alan A. Schneider, Reisterstown, Md.

[73] Assignee: Catalyst Research Corporation, Baltimore, Md.

[21] Appl. No.: 972,735

[22] Filed: Dec. 26, 1978

[51] Int. Cl.² ............................................. G01N 27/46
[52] U.S. Cl. ................................. 204/195 P; 204/1 T
[58] Field of Search ............... 204/1 F, 195 P; 324/29

[56] References Cited

U.S. PATENT DOCUMENTS

| | | | |
|---|---|---|---|
| 3,857,760 | 12/1974 | Breuer et al. | 204/1 T |
| 4,001,103 | 1/1977 | Blurton et al. | 204/195 R |
| 4,049,503 | 9/1977 | Becker et al. | 204/1 T |
| 4,051,006 | 9/1977 | Neti et al. | 204/195 P |
| 4,092,232 | 5/1978 | Zetter | 204/195 P |

Primary Examiner—G. L. Kaplan
Attorney, Agent, or Firm—Reed, Smith, Shaw & McClay

[57] ABSTRACT

An electrochemical cell for the detection of hydrogen sulfide which includes a gold working electrode and a counter electrode, with or without a reference electrode, comprising either gold or platinum black which operate in a substantially non-aqueous electrolyte consisting preferably of lithium perchlorate dissolved in an organic solvent selected from the group consisting of γbutyrolactone and propylene carbonate. A fixed potential is maintained between the working electrode and a referenced air electrode of between 300 to 1100 mv, and, preferably, between 500 and 1000 mv.

13 Claims, 4 Drawing Figures

ELECTROCHEMICAL CELL FOR THE DETECTION OF HYDROGEN SULFIDE

FIELD OF THE INVENTION

The present invention relates to an electrochemical cell suitable for use in detecting and measuring hydrogen sulfide in which a substantially non-aqueous organic electrolyte is used.

BACKGROUND OF THE INVENTION

The need for detecting and measuring gaseous components of the environment has been increased because of regulations which deal with clean air, clean water and a clean work place. Numerous devices have been produced to measure such gaseous components one of which operates on electrochemical principles. Many electrochemical processes for the determination of gaseous components are known in the art. See for example *Advances in Electrochemistry and Electrochemical Engineering*, Volume 10, (J. Wiley & Sons, 1976).

Of particular importance in any electrochemical detecting sensor is that it have high accuracy, good reproductability, high sensitivity to the gas sought to be measured and little interference from other gaseous components of the environment. And, in the case of threshold limiting value (TLV) measurements, a fast response time. Presently, most electrochemical sensors operate in an aqueous electrolyte, see for example U.S. Pat. Nos. 3,776,832 and 3,992,267. The most commonly used aqueous electrolytes incorporate solutions of sulfuric acid because of their insensitivity to carbon dioxide which is frequently present in gaseous mixtures. Unfortunately, aqueous electrolytes are restricted by the range of electrical potential at which water decomposes and by the high vapor pressure of water. Aqueous electrolytes also have a very high dielectric constant and, therefore, can generally dissolve more gas. However, such high dissolution rates also create various measurement distortions.

Prior to the present invention, electrochemical cells using an aqueous electrolyte were sensitive to the humidity in the air to be measured. Such cells required a water humidifier to maintain the level of electrolyte. The present invention is directed to an electrochemical cell in which a substantially non-aqueous organic electrolyte is used to sense and measure $H_2S$. It is an object of the present invention to provide an electrochemical cell which is extremely accurate, has a fast response time, and can be used continuously without maintaining the electrolyte level.

SUMMARY OF THE INVENTION

Generally, the present invention comprises an electrochemical cell having a housing preferably made from polyethylene or other plastic material which is resistant to the electrolyte, nonabsorbent and inert with respect to $H_2S$. The cell includes therethrough a coextensive cavity for receiving an organic electrolyte. Sealingly positioned across one end of the cavity is a working electrode consisting of a gas diffusion membrane having a first gold catalytic member positioned on the cavity side thereof and electrically connected to a detecting circuit. Preferably, the working electrode is prepared by mixing gold powder with a TFE dispersion and painting the mixture onto a Zitex ® (a porous fluorocarbon) which acts as the membrane material. The membrane and electrode are dried and sintered to obtain and achieve a good bond.

A counter electrode is sealingly positioned across the other end of the cavity. The counter electrode comprises a gas diffusion membrane having a second catalytic member preferably consisting of gold or platinum black positioned on the cavity side to which an electrical lead is connected. Preferably, the counter electrode includes an air reference electrode to which an electrical lead is connected thereto for maintaining the working electrode at the desired potential. The counter and reference electrodes are typically Teflon ® bonded platinum black electrodes which are dispersion painted onto a Zitex ® membrane, dried and sintered in the same manner as the working electrode.

Generally, it is desirable to include first and second end plates which are sealingly positioned across the respective ends of the housing. The first end plate is spaced away from the working electode to provide a chamber adjacent thereto and includes a gas inlet for directing gas to be detected and measured to the membrane of the working electrode. Each plate is mounted by means of bolts which most advantageously pass through the housing and both end plates and are made from the same material. In applications where end plates are not desired, such as in small portable units, the membranes are exposed to the atmosphere and define the ends of the cell.

An electrolyte consisting of one molar lithium perchlorate dissolved in an organic solvent which is selected from the group consisting of $\gamma$-butyrolactone and propylene carbonate fills the cavity. Preferably, lithium perchlorate is dissolved in propylene carbonate which is slightly hydrophilic and maintains the solution with about 1 percent water. It is understood, however, that other inorganic salts which provide some ionic conductivity and which are soluble in the organic solvent and are nonreactive to the electrodes or with the solvent at the operating potentials uses are suitable for use in the present invention.

In a preferred embodiment of the invention, the cell comprises a third (reference) electrode which is useful for maintaining the potential difference between such reference electrode and the working electrode from between 300 to 1100 mv. For best results, it has been found that the potential should be maintained between about 500 to 1000 mv and preferably about 700 mv with reference to the platinum air electrode. However, in order to adjust for the optimum efficiency, e.g. response time, stability, interferences and zero current, it may be desirable to potentiostat the cell. In the measurement of $H_2S$, the present cell is sensitive to temperature variations and should include temperature compensation for both the zero current and span current. Compensation is preferably provided by means of compensating circuits such as those described in U.S. application Ser. No. 970,334 filed (12/18/78) owned by the assignee of the present invention.

The present invention provides a generally linear response from about 0 to 50 parts per million $H_2S$ with response time to the gas in about 30 seconds to a couple of minutes. Typically, cells of the present invention provide a 4 to 10 $\mu A$/ppm output response. Other advantages will become apparent from a perusal of the following detailed description of the best mode for making and practicing the present invention taken in connection with the accompanying drawings.

DETAILED DESCRIPTION OF THE INVENTION

Figure 1:
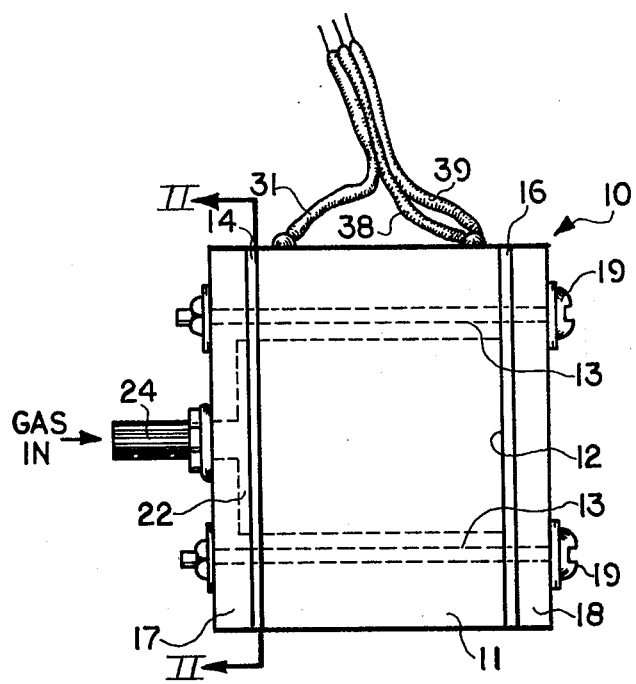
FIG. 1 is an elevation of the electrochemical cell of the present invention.

The following is a detailed description of the best mode presently contemplated for the manufacture and use of the electrochemical cell of the present invention. With respect to FIG. 1, electrochemical cell 10 comprises housing 11 having a cavity 12 coextensively positioned therethrough. Housing 11 includes openings 13 to receive mounting bolts 19 and is preferably formed from a solid block of polyethylene such that cavity 12 may be easily formed by drilling through the block. As should be clear, however, the particular form or configuration of the housing or arrangement and configuration of the electrodes can be altered to suit the final instrument package into which the electrochemical cell is to be adapted.

Cell 10 includes working electrode 14 and counter/reference electrodes 16, described more fully below. Electrodes 14 and 16 are sealingly mounted at opposite ends of housing 11 by respective end plates 17 and 18. End plates 17 and 18 are secured to housing 11 by means of bolts 19 which pass through openings 13 in housing 11 and correlative openings 21 in electrodes 16 and 14. End plate 17 includes recess 22 to provide for sufficient area for diffusion of the gas into the membrane of the working electrode. Alternatively, sufficient space can be obtained by means of annular sealing means (not shown) such as an "O" ring which is preferably positioned between the end plate and working electrode. With respect to the reference air electrode, it has not been found necessary to provide a similar recess since sufficient air enters through the membrane exposed at the periphery of housing 11 and end plate 18.

End plate 17 also includes gas inlet 24 which in typical detection instruments is connected to a means for pumping environmental or atmospheric air into the cell at a closely controlled rate and an outlet 25. The atmospheric air enters into and through the chamber formed by recess 22 and working electrode 14 and diffuses into the electrolyte contained in cavity 12 through the membrane portion of electrode 14. As mentioned above, sufficient air diffuses through the Zitex® membrane to supply oxygen to counter/reference electrodes 16 which functions as the air electrodes in the preferred embodiment.

Figure 2:
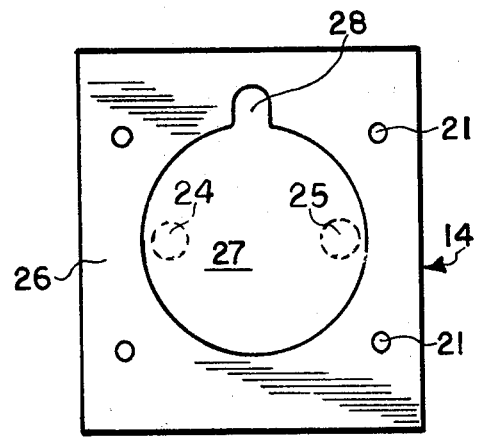
FIG. 2 is an elevation along line II—II of FIG. 1 showing the working electrode bonded to Zitex® membrane.
Figure 3:
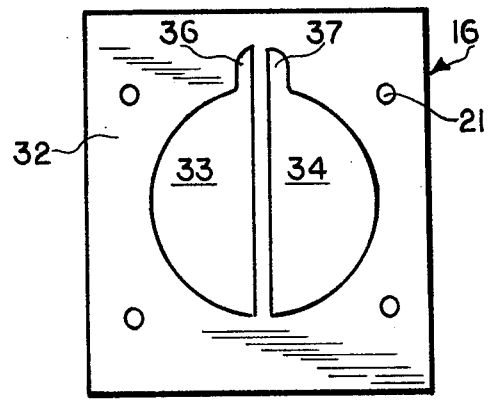
FIG. 3 is a front elevation of a counter and a reference electrode bonded to a Zitex® membrane.

Referring to FIGS. 2 and 3 working electrode 14 comprises a Zitex® or Gortex® (porous fluorocarbon) membrane 26. Any other membrane material may be used. Such other material would most desirably have characteristics similar to Zitex®, such as not becoming wetted by the electrolyte, large number of pores (e.g. 50% porous) having a small pore size, thin enough to avoid restricting the concentration of gas and nonreactive with the gas and solvent. Most importantly, it must permit diffusion of the desired gas without allowing the electrolyte to escape. Preferably membrane 26 is of the same basic configuration as housing 11 and includes openings 21 which cooperate with openings 13 to receive bolts 19. Working electrode 14 also includes catalyst portion 27 having a configuration and shape substantially the same as cavity 12 and preferably consisting of a high gold powder surface area (0.61 sq in) (e.g. 45 mg) (0.4 m²/gm) and TFE (Teflon®) dispersion (e.g. 30% Teflon®/70% water solution) sintered to membrane 26. In the manufacture of the electrodes, it is desirable to add the dispersion to the gold powder which had already been placed on the membrane. Catalyst portion 27 also includes tab 28 to which is electrically connected lead 31 (See FIG. 1).

Counter/reference electrode 16 includes membrane 32 made of Zitex® or Gortex® and a catalytic portion. In the case of a two electrode cell, the catalytic portion of the electrode structure would be manufactured in a manner similar to that of the working electrode, except it is preferable ot use platinum black instead of gold. In the preferred embodiment, however, the catalytic portion is divided into first region 33 defining the counter electrode having an area of about 1.2 sq. inches and second region 34 defining the reference electrode having an area of about 1.2 sq. inches. Each region includes an associated tab 36 and 37 for connection with electrical leads 38 and 39. First and second regions of the catalyst portion preferably consists of Teflon® bonded platinum black (e.g. 35 mg each) sintered to membrane 32.

The electrolyte solution preferably comprises either propylene carbonate or $\beta$-butyrolactone into which is dissolved lithium perchlorate or other suitable supporting electrolyte. The lithium perchlorate is present in an amount of from $10^{-5}$ molar to saturated and preferably from 0.1 to 1.0 molar.

Figure 4:
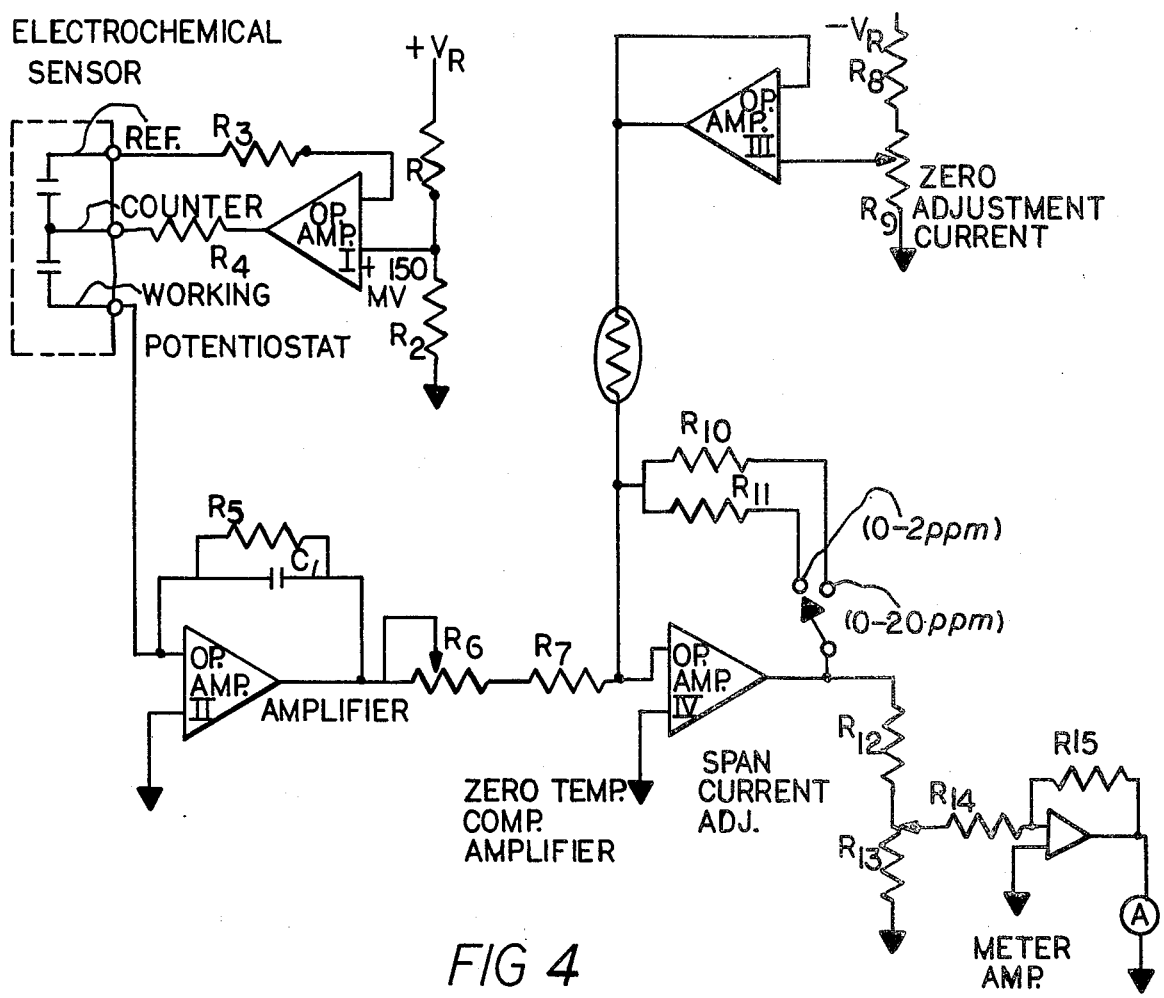
FIG. 4 is a circuit diagram useful in detecting and measuring H₂S gas with the cells of the present invention.

The electrical circuit for use in converting the output of the cell need only include a voltmeter with parallel resistors in the case of a two electrode cell as is well known in the art. In the three electrode cell, however, it is desirable to potentiostat the cell for optimum efficiency. Because cells of the present invention provide erroneous output signals due to temperature variations between 35° and 50° C., a temperature compensation circuit is required for both span and zero currents. As shown in schematic diagram shown in FIG. 4, a thermistor Th₁ is used to compensate for both span and zero current and thermistor Th₂ is used to compensate for zero current error. The compensated error is about $-0.13$ ppm/°C. at $-35°$ C. to $+0.5$ ppm/°C. at 40° C. With respect to a three electrode cell, FIG. 4 is a schematic diagram of a circuit useful in converting the signals from the cells of the present invention into two concentration ranges of H₂S.

In a presently preferred embodiment the values in ohms of the resistors are as follows:

Potentiostat: Op. Amp Fairchild 747A, $R_1 = 10K$, $R_2 = 1.3K$, $R_3 = 750$ and $R_4 = 100$.

OPERATIONAL AMPLIFIER II and CIRCUIT: RCA 3160, $R_5 = 8.06K$, $R_{51} = 4750$ $C_1 = 0.01$ $\mu f$ at 6 volts and Thermistor $Th_1 = 5K$ at 25° C.

CALIBRATION: $R_6 = 10K$ and $R_7 = 5K$.

ZERO CURRENT ADJUST. CIRCUIT: OP Amp Fairchild 747B, $R_8 = 13.3K$, $R_9 = 5K$.

THERMISTOR $Th_2$: 30K at 25° C.

OP. AMP. IV CIRCUIT: RCA 3160, $R_{10} = 2.5K$, $R_{11} = 10K$.

SPAN ADJUST.: $R_{12} = 499K$, $R_{13} = 5K$.

METER AMP.: $R_{14}=100K$, $R_{15}=200K$.

Table I below shows the response time of three cells for a step change from 3.5 to 7 ppm of $H_2S$ at a flow rate of 200 cc/min.

TABLE I

| CELL NO. | 90% UP | 90% DOWN | 80% UP | 80% DOWN | 70% UP | 70% DOWN |
|---|---|---|---|---|---|---|
| 1 | 1 min. 45 sec. | * | 50 sec. | * | 25 sec. | 3 min. |
|   | 40 sec. | 3 min. 45 sec. | 30 sec. | 45 sec. | 15 sec. | 15 sec. |
| 2 | 6 min. | * | 3 min. 15 sec. | * | 2 min. 15 sec. | 6 min. 40 sec. |
|   | 3 min. | 6 min. | 1 min. 30 sec. | 3 min. 25 sec. | 1 min. 25 sec. | 1 min. 45 sec. |
| 3 | 3 min. 40 sec. | * | 1 min. 30 sec. | 2 min. 15 sec. | 45 sec. | 50 sec. |
|   | 3 min. | 3 min. 40 sec. | 2 min. 15 sec. | 2 min. 15 sec. | 1 min. | 1 min. 30 sec. |

* Not Available

Table II shows the interferring effect of various compounds normally found in the environment in which hydrogen sulfide measurements are made.

TABLE II

| GAS | PPM EXPOSED | EQUIVALENT TO 1 PPM $H_2S$ |
|---|---|---|
| $SO_2$ | 9.9 | 24 |
| $NH_3$ | 45.0 | 5 |
| $Cl_2$ | 5.0 | −29 |
| CO | 47.0 | 725 |
| HCN | 14 | 145 |
| $NO_2$ | 94 | 29 |
| NO |  | 4 |
| Acetylene | 10 | 10 |
| Ethylene |  | 1 |
| Propane |  | 5 |
| Methane | 20,000 | >20,000 |
| Hydrogen |  | 40 |
| Pentanethiol (n = amyl mercaptan) |  | 750 |
| Methyl 2-propanethiol (tert-butyl mercaptan) |  | 750 |

Cells of the present invention have a low detectability level of about 0.1 ppm $H_2S$ and are preferably operated in a range of from 0 to 20 ppm $H_2S$. It is contemplated that the average life of the cells will be in excess of one year. Table III shows the results of age tests conducted on 10 cells of the present invention.

TABLE III $H_2S$ AGE TESTING

| CELL NO. | DATE MADE | DATE TESTED | OUTPUT μA/PPM | DATE TESTED | OUTPUT μA/PPM | DATE TESTED | OUTPUT μA/PPM | DATE TESTED | OUTPUT μA/PPM |
|---|---|---|---|---|---|---|---|---|---|
| 1 | 5/27/77 | 12/29/77 | 8.40 | 3/14/78 | Failed |  |  |  |  |
| 2 | 6/29/77 | 12/29/77 | 5.73 | 3/13/78 | 5.00 | 6/02/78 | 10.1 |  |  |
| 3 | 8/31/77 | 12/29/77 | 1.74 | 2/10/77 | 2.81 | 3/13/78 | 2.87 |  |  |
| 4 | 9/12/77 | 12/29/77 | 1.42 | 3/13/78 | 0.38 | 6/02/78* | 1.50 |  |  |
| 5 | 10/07/77 | 12/29/77 | 3.74 | 3/13/78 | 5.26 | 6/02/78 | 3.60 |  |  |
| 6 | 10/17/77 | 12/29/77 | 5.20 | 3/14/78 | 6.03 | 6/02/78 | 3.34 |  |  |
| 7 | 10/17/77 | 12/29/77 | 2.91 | 3/14/78 | 3.29 | 6/02/78 | 2.80 |  |  |
| 8 | 1/23/78 | 1/24/78 | 3.95 | 3/14/78 | 3.65 | 5/25/78 | 2.60 |  |  |
| 9 | 1/23/78 | 1/24/78 | 2.23 | 2/09/78 | 1.87 | 5/25/78 | 3.10 |  |  |
| 10 | 1/23/78 | 1/26/78 | 1.85 | 1/31/78 | 1.42 | 3/14/78 | 1.73 | 5/25/78 | 2.20 |

*High Zero current, approximately 60 μA

While a presently preferred embodiment of the invention has been shown and described, the invention may be otherwise embodied within the scope of the appended claims.

What is claimed is:

1. An electrochemical cell for use in detecting $H_2S$ gas comprising:
   a. first and second spaced apart electrodes, each of said electrodes consisting of a gas permeable membrane having bonded thereto a catalyst portion consisting essentially of gold for said first electrode and gold or platinum black for said second electrode, said catalyst portions being positioned to face each other;
   b. an electrolyte contained between said electrodes and in contact with the catalyst portion and membrane of each said electrodes, said electrolyte consisting of a solvent selected from the group consisting of propylene carbonate and γ-butyrolactone, and from $10^{-5}$ molar to satuation of an inorganic salt;
   c. means for containing said electrolyte and said electrodes; and
   d. means for maintaining a fixed potential of the first electrode with respect to the second electrode of between 300 and 1100 mv.

2. An electrochemical cell as set forth in claim 1 wherein said second electrode consists essentially of platinum black and said inorganic salt is lithium perchlorate.

3. An electrochemical cell as set forth in claim 2 wherein said means for containing the electrolyte and electrodes comprises a housing having an electrolyte receiving cavity coextensively positioned therethrough and end plates for sealingly positioning said electrodes at respective ends of the cavity.

4. An electrochemical cell as set forth in claim 2 wherein said second electrode includes first and second catalyst portions.

5. An electrochemical cell as set forth in claim 1 wherein said membranes of the first and second electrode are a porous flourocarbon.

6. An electrochemical cell as set forth in claim 1 wherein said means for maintaining a fixed potential of the first electrode maintains said potential between 500 and 1000 mv.

7. An electrochemical cell as set forth in claim 1 wherein said means for maintaining the fixed potential of the first electrode maintains said potential at 700 mv.

8. An electrochemical cell for use in sensing hydrogen sulfide gas comprising:
   a. a housing having cavity coextensive therethrough for receiving an electrolyte;
   b. a working electrode sealingly positioned across one end of said cavity and consisting of a gas diffusion membrane having a first gold catalytic member positioned on the cavity side of said membrane and an electrical lead connected to said first catalytic member;
c. a counter electrode sealingly positioned across the other end of said cavity and consisting of a gas diffusion membrane having a second catalytic member consisting of gold or platinum black positioned on the cavity side thereof and an electrical lead connected to said second catalytic member;
d. an electrolyte consisting of from 0.1 to 1.0 molar of lithium perchlorate dissolved in an organic solvent selected from the group consisting of γ-butyrolactone and propylene carbonate; and
e. means for maintaining potential of the working electrode with respect to the counter electrode between 500 and 1000 mv.

9. An electrochemical cell as set forth in claim 8 wherein said means for maintaining the fixed potential of the working electrode maintains said potential at 700 mv.

10. An electrochemical cell as set forth in claim 8 wherein said housing includes first and second end plates sealingly positioned on respective ends of said housing, said first end plate being spaced apart from the working electrode and including a gas inlet.

11. An electrochemical cell as set forth in claim 8 wherein said counter electrode includes a third catalytic member consisting of gold or platinum black and an electrical lead connected to said third catalytic member.

12. An electrochemical cell as set forth in claim 11 wherein said means for maintaining the potential of the working electrode maintains said potential fixed with respect to said reference electrode at between about 500 to 1000 mv.

13. An electrochemical cell as set forth in claim 12 wherein said potential is fixed at 700 mv.

* * * * *

UNITED STATES PATENT AND TRADEMARK OFFICE
CERTIFICATE OF CORRECTION

PATENT NO. : 4,169,779

DATED : October 2, 1979

INVENTOR(S) : Harshad Tataria, et al.

It is certified that error appears in the above-identified patent and that said Letters Patent are hereby corrected as shown below:

Column 4, line 32, after "or" delete β-butyrolactone and substitute therefor -- γ-butyrolactone --.

Signed and Sealed this

Fourth Day of December 1979

[SEAL]

Attest:

SIDNEY A. DIAMOND

Attesting Officer

Commissioner of Patents and Trademarks